(12) United States Patent
Bokhove et al.

(10) Patent No.: US 12,344,833 B2
(45) Date of Patent: *Jul. 1, 2025

(54) METHOD FOR SEPARATING BIOMASS FROM SOLID FERMENTATION PRODUCT

(71) Applicant: PURAC Biochem BV, Gorinchem (NL)

(72) Inventors: Jeroen Bokhove, Gorinchem (NL); Andre Banier De Haan, Gorinchem (NL); Willem Jacob Groot, Gorinchem (NL)

(73) Assignee: PURAC Biochem BV, Gorinchem (NL)

( * ) Notice: Subject to any disclaimer, the term of this patent is extended or adjusted under 35 U.S.C. 154(b) by 394 days.

This patent is subject to a terminal disclaimer.

(21) Appl. No.: 17/662,553

(22) Filed: May 9, 2022

(65) Prior Publication Data
US 2022/0259549 A1 Aug. 18, 2022

Related U.S. Application Data

(63) Continuation of application No. 16/304,959, filed as application No. PCT/EP2017/062919 on May 29, 2017, now Pat. No. 11,352,600.

(30) Foreign Application Priority Data

May 30, 2016 (EP) .................................. 16172032

(51) Int. Cl.
*C12N 1/02* (2006.01)
*C12P 7/56* (2006.01)

(52) U.S. Cl.
CPC . *C12N 1/02* (2013.01); *C12P 7/56* (2013.01)

(58) Field of Classification Search
CPC ...... C12N 1/02; C12P 7/56; C12P 7/46; C12P 7/40; C12P 17/04; Y02E 50/10
See application file for complete search history.

(56) References Cited

U.S. PATENT DOCUMENTS

| | | | |
|---|---|---|---|
| 11,352,600 B2 * | 6/2022 | Bokhove | .................. C12N 1/02 |
| 2015/0314217 A1 | 11/2015 | Koch et al. | |

FOREIGN PATENT DOCUMENTS

| | | | | |
|---|---|---|---|---|
| JP | H06154643 A | 6/1994 | | |
| JP | 2015514432 A | 5/2015 | | |
| WO | WO-2013160352 A1 * | 10/2013 | ............ | C12M 47/10 |
| WO | WO2013062407 A1 | 5/2014 | | |
| WO | WO-2016016233 A1 * | 2/2016 | ................ | C12P 7/56 |

OTHER PUBLICATIONS

International Search Report and Written Opinion; Mailed Jun. 29, 2017 for PCT Application No. PCT/EP2017/062919.
Juturu, Veeresh, and Jin Chuan Wu. "Microbial production of lactic acid: the latest development." Critical reviews in biotechnology 36.6 (2016): 967-977.
Wang, Yong, et al. "Efficient magnesium lactate production with in situ product removal by crystallization." Bioresource technology 198 (2015): 658-663.
Daful, Asfaw Gezae, and Johann F. Goergens. "Techno-economic analysis and environmental impact assessment of lignocellulosic lactic acid production." Chemical Engineering Science 162 (2017): 53-65.
Li, Qian-Zhu, et al. "Recovery processes of organic acids from fermentation broths in the biomass-based industry." J Microbiol Biotechnol 26.1 (2016): 1-8.
Matsumoto, M., et al. "Extractive fermentation of lactic acid with Hiochi bacteria in a two-liquid phase system." Ferment Technol 5 (2016): 1-6.
Notice of Reasons for Rejection for corresponding Japanese application No. 2018-562091; dated Dec. 24, 2019 (11 pages).
Office Action for corresponding Korean application No. 10-2018-7037791; dated Feb 12, 2020 (12 pages).

* cited by examiner

*Primary Examiner* — Robert B Mondesi
*Assistant Examiner* — Alexander B Pastora
(74) *Attorney, Agent, or Firm* — Sunit Talapatra; Foley & Lardner LLP

(57) ABSTRACT

A method for separating biomass from solid fermentation product is provided. According to the method, a slurry comprising biomass and solid fermentation product is provided to the top of a biomass separator unit and an aqueous medium is provided to the bottom of a biomass separator unit, while a product stream comprising solid fermentation product is withdrawn from the bottom of the biomass separator unit and a waste stream comprising biomass is withdrawn from the top of the biomass separator unit.

20 Claims, 1 Drawing Sheet

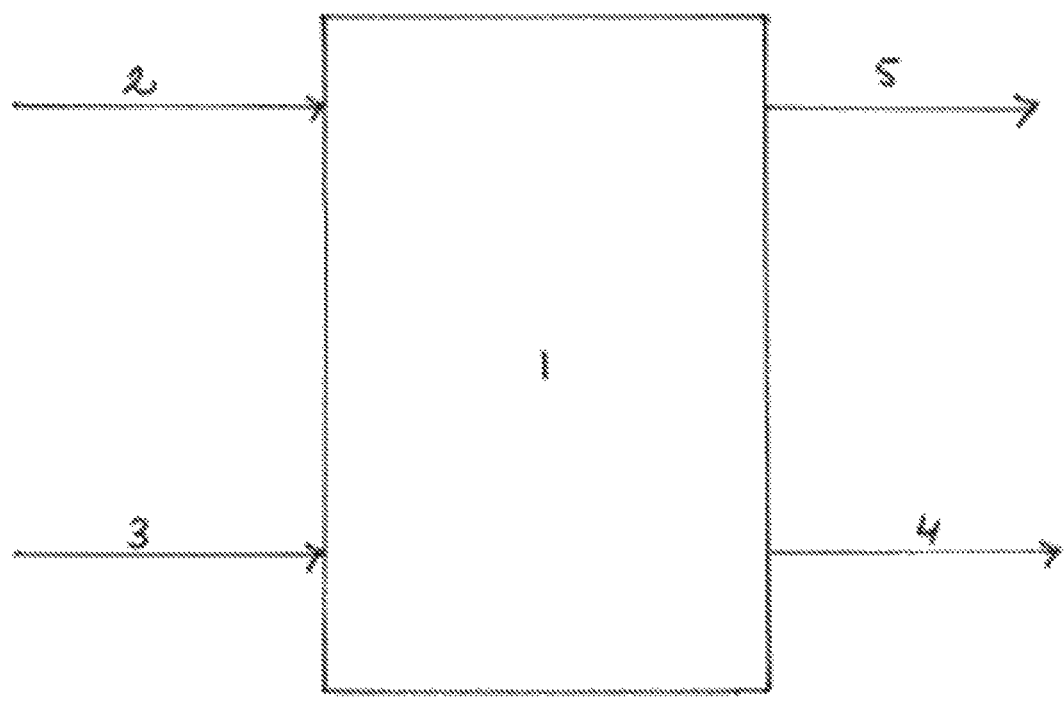

METHOD FOR SEPARATING BIOMASS FROM SOLID FERMENTATION PRODUCT

CROSS-REFERENCE TO RELATED APPLICATIONS

This application is a continuation of U.S. patent application Ser. No. 16/304,959, filed on Nov. 27, 2018, issued as U.S. Pat. No. 11,352,600 on Jun. 7, 2022, which, in turn is a 371 continuation of PCT/EP2017/062919, filed on May 29, 2017, now expired, which, in turn, claims priority to European patent application no. 16172032.1, filed on May 30, 2016, the disclosures of which are hereby incorporated by reference in their entirety as if full set forth herein.

FIELD OF THE INVENTION

The invention pertains to a method for separating biomass from solid fermentation products.

BACKGROUND OF THE INVENTION

In a fermentation process, a carbon source is fermented using a microorganism to produce a desired compound. Fermentation processes are attractive because they allow the manufacture of a wide variety of compounds from renewable resources. However, an issue with fermentation processes is the purification of the resulting product. The desired compound will be present in a fermentation broth which comprises, in addition to the desired compound, also numerous further compounds such as the microorganisms who produced the desired compounds, side products, nutrients and remains of the carbon source.

A particular issue has been found to reside in the separation of biomass, which is a term used to indicate the microorganisms used in the fermentation, from a solid fermentation product. It has been found that a high efficiency of biomass removal is required to prevent the formation of undesired contaminants during further processing of solid fermentation product. It has also been found that it is often difficult to obtain the required high efficiency, since biomass is also a solid product, which tends to follow the solid fermentation product.

WO2013/160352 describes a fermentation process wherein a fermentation broth comprising biomass and a solid fermentation product, in that case a salt of an organic acid, is withdrawn from a fermentation reactor and provided to a hydrocyclone. The bottom effluent from the hydrocyclone comprises solid fermentation product, and is provided to a solid-liquid separation step to separate the solid fermentation product from the liquid. It is indicated that the use of a belt filter has been found to be advantageous, because it has a high wash efficiency, allowing efficient removal of biomass and solid and dissolved contaminants and obtaining a filter cake with a relatively low water content and a relatively low content of contaminant products. It is indicated that the belt filter can be equipped with means for washing the filter cake to improve separation, including means for reslurrying the filter cake.

It has been found that the use of belt filter has various disadvantages. It is difficult to remove the last fractions of biomass using a belt filter. Further, if this is attempted, e.g., by repeated washing of the filter cake, this results in an complicated process, which may be associated with substantial loss of desired product. Therefore, there is need in the art for a method for separating biomass from solid fermentation product which allows an efficient separation of biomass from a solid fermentation product, while product loss can be minimized. This problem is solved by the present invention.

SUMMARY OF THE INVENTION

The invention pertains to a method for separating biomass from solid fermentation product wherein a slurry comprising biomass and solid fermentation product is provided to the top of a biomass separator unit and an aqueous medium is provided to the bottom of a biomass separator unit, while a product stream comprising solid fermentation product is withdrawn from the bottom of the biomass separator unit and a product stream comprising biomass is withdrawn from the top of the biomass separator unit.

In one aspect, the invention relates to a method for separating biomass from solid fermentation product wherein an aqueous slurry comprising biomass and solid fermentation product is provided to the top of a biomass separator unit and an aqueous medium is provided to the bottom of a biomass separator unit, while a product stream comprising solid fermentation product is withdrawn from the bottom of the biomass separator unit and a waste stream comprising biomass is withdrawn from the top of the biomass separator unit.

In the foregoing method, the slurry may comprise biomass and solid fermentation product comprises at least 10 wt. % of solid fermentation product, in particular at least 30 wt. %, more in particular at least 40 wt. %, and/or at most 70 wt. %, in particular, at most 60 wt. %.

In each of the foregoing methods, the amount of biomass present in the slurry may be in the range of 0.05 to 5 wt. %.

In each of the foregoing methods, the amount of biomass present in the slurry is may be in the range of 0.05 to 1.5 wt. %, in particular, 0.05 to 1 wt. %, more in particular 0.05 to 0.8 wt. %.

In each of the foregoing methods, the biomass separator unit may be provided with static and/or dynamic mixing elements.

In each of the foregoing methods, the aqueous medium provided to the bottom of the biomass separator unit may be a solution of fermentation product, wherein the solution preferably has a concentration of at least 50% of the saturation concentration, in particular at least 70%, more in particular at least 80%, or even at least 90%.

In each of the foregoing methods, the waste stream withdrawn from the top of the biomass separator unit may be subjected to a biomass removal step and the remaining solution is recycled as aqueous medium to the bottom of the biomass separator unit.

In each of the foregoing methods, the solid fermentation product may be selected from salts of carboxylic acids, in particular magnesium lactate, magnesium succinate, magnesium furandicarboxylate, calcium lactate, calcium succinate, and calcium furandicarboxylate, more in particular magnesium lactate.

In each of the foregoing methods, the solid fermentation product in the product stream may be subjected to a purification step resulting in a purified solid fermentation product.

In each of the foregoing methods, the solid fermentation product may be a salt of a carboxylic acid, and the method comprises the step of converting the salt of a carboxylic acid into the corresponding carboxylic acid to form a carboxylic acid and an inorganic salt.

In the foregoing embodiment, the carboxylic acid may be separated from the inorganic salt and the carboxylic acid may be optionally subjected to one or more purification steps resulting in the formation of a purified carboxylic acid.

In each of the foregoing methods, the solid fermentation product may be a solid lactic acid salt, the solid lactic acid salt is converted to lactic acid, the lactic acid is subjected to one or more of a purification step, a crystallisation step or an oligomerisation step resulting in the formation of lactic acid oligomers, or converted to lactide, or to polylactic acid, either directly or via lactide.

It has been found that the method according to the invention makes it possible to provide a solid fermentation product which comprises very low amounts of remaining biomass, while product loss can be limited. Further advantages of the present invention and of the various embodiments thereof will become apparent from the further specification.

The invention will be discussed in more detail below. The FIGURES illustrate various aspects of the present invention, but the present invention is not limited thereto or thereby.

BRIEF DESCRIPTION OF THE DRAWING

FIG. 1 illustrates a first embodiment of the present invention.

DETAILED DESCRIPTION OF THE EMBODIMENTS

In FIG. 1, a slurry comprising biomass and solid fermentation product is provided through line (2) to the top of a biomass separator unit (1). An aqueous medium is provided through line (3) to the bottom of the biomass separator unit (1). A product stream comprising solid fermentation product is withdrawn from the bottom of the biomass separator unit (1) through line (4) and a waste stream comprising biomass is withdrawn through line (5) from the top of the biomass separator unit (1).

The starting material in the present invention is an aqueous slurry comprising biomass and solid fermentation product. Within the context of the present specification, a solid fermentation product is a product resulting from a fermentation which is present in solid form in an aqueous medium. In other words, a solid fermentation product is a fermentation product which is present in the aqueous medium in a concentration above its saturation concentration.

The nature of the solid fermentation product is generally not critical to the present invention. In one embodiment, the solid fermentation product is a salt of a carboxylic acid. Solid salts of carboxylic acids and methods for obtaining them will be described in more detail below.

The solid fermentation product may be a crystalline product or an amorphous product. It will generally be a crystalline product.

The slurry as provided to the biomass separator unit generally comprises 5-70 wt. % of solid fermentation product. If the amount of solid fermentation product is very low, the biomass separator unit will have to be relatively large to accommodate the large slurry volumes. On the other hand, if the amount of solid fermentation product is very high, the processability, e.g., the pumpability of the slurry may decrease. Further, efficient removal of biomass may be prevented. It may be preferred for the reasons given above for the amount of solid fermentation product to be at least 10 wt. %, in particular at least 20 wt. %, in some embodiments at least 30 wt. %, specifically at least 40 wt. %. On the other hand, to ensure efficient biomass separation and processing, it may be preferred for the amount of solid fermentation product in the slurry to be at most 60 wt. %.

For magnesium lactate as fermentation product, it may be preferred for the amount of solid fermentation product in the slurry to be in the range of 30-60 wt. %, in particular 40-60 wt. %, e.g., in the range of 45-55 wt. %.

The slurry can be derived directly from the fermentation unit. It is also possible for the slurry derived from the fermentation unit to first be subjected to one or more concentration steps in which water is removed. Concentration can be carried out by methods known in the art, e.g., using settlers, hydrocyclones, or other measures.

The amount of biomass present in the slurry may vary within wide ranges, depending on whether biomass was also removed in preceding steps. As a general guideline a range of 0.05 to 5 wt. % may be given.

In one embodiment of the present invention, the biomass content of the slurry is relatively low. This can, e.g., be the case where the fermentation broth has already been subjected to a step in which biomass has been partially removed. In this case, the amount of biomass may, e.g., be in the range of 0.05 to 1.5 wt. %, in particular, 0.05 to 1 wt. %, more in particular 0.05 to 0.8 wt. %.

The amount of biomass in a slurry can be determined, e.g., by determining the optical density at 600 nm of a sample from which crystals have been removed, and comparing it with the OD600 nm of standard biomass solutions.

The slurry comprising biomass and solid fermentation product is provided to the top of a biomass separator unit. As will be clear to the skilled person, in the present specification the indication top refers to a location in the upper part of the biomass separator unit, above the separation section. In the biomass separator unit, the aqueous slurry is contacted in countercurrent operation with an aqueous medium provided to the bottom of the biomass separator unit. Not wishing to be bound by theory it is believed that the biomass particles are entrained by the flow of the aqueous medium, which is from the bottom of the unit to the top of the unit, resulting in a product stream comprising biomass. This stream is withdrawn from the top of the biomass separator unit. The solid fermentation product has a higher density than the biomass. It is therefore not entrained in the aqueous medium, and can be withdrawn from the bottom of the unit.

The biomass separator unit is in essence a column which is equipped so that the slurry containing biomass and solid fermentation product comes into intimate contact with the aqueous medium. In one embodiment, the unit is equipped with mixing elements to improve contact and to disperse optional aggregates of biomass and/or solid fermentation product. Mixing elements may be static mixing elements, such as rods or strips. Mixing elements may also be dynamic mixing elements such as one or more agitators.

The composition of the aqueous medium provided to the separator unit in in general not critical, as long as it does not contain compounds which are undesirable if they end up in the end product. Water is of course a suitable medium. In a preferred embodiment, however, the aqueous medium is a solution of the solid fermentation product. If a solution of solid fermentation product is used, in particular a solution which is saturated or almost saturated, the yield of the process will be improved, as product loss through dissolving of solid fermentation product in the aqueous medium will be limited. In one embodiment, the aqueous medium therefore is a solution of fermentation product, wherein the solution has a concentration of at least 50% of the saturation concentration, in particular at least 70%, more in particular at least 80%, or even at least 90%. In this context, the saturation concentration is defined as the maximum concentration of fermentation product which can be dissolved in the aqueous medium under the conditions prevailing in the medium when it is provided to the separator unit. The aqueous medium can in principle contain solid particles of fermentation product, but this is generally not desired. Therefore, in one embodiment, the aqueous medium comprises at most 110% of the saturation concentration of the fermentation product.

As will be discussed below, the aqueous medium can be obtained by removing biomass from the waste stream containing biomass which is withdrawn from the top of the unit. The aqueous medium can also be obtained from other sources, e.g., from downstream processing steps where saturated solutions of solid fermentation product are obtained.

The volume of aqueous medium provided to the unit within a specific period of time will depend on the volume of the slurry comprising fermentation medium and solid fermentation product provided in that period of time. In general, the volume of the aqueous medium provided to the unit is between 10 and 500 vol. % of the volume of the slurry provided to the unit, more specifically between 50 and 250 vol. %. Higher volumes of aqueous medium require a larger biomass separator unit. On the other hand, the use of a higher volume of aqueous medium may result in a more thorough biomass removal. It may be preferred for the volume of the aqueous medium provided to the unit to be between 60 and 100 vol. % of the volume of the slurry provided to the unit.

A product stream comprising solid fermentation product is withdrawn from the bottom of the biomass separator unit. In general, the concentration of solid fermentation product in this bottom product stream will be in the same range as the concentration of fermentation product in the feed stream. For general ranges reference is thus made to what is stated above.

The biomass content of the product stream is substantially reduced as compared to the biomass content of the starting slurry. It is preferred for at least 70% of the biomass to be removed, in particular at least 80%, more in particular at least 90%. It has been found that it is possible to remove at least 95% of biomass, in particular at least 98%. It has been found possible, and preferred, to remove at least 99% of the biomass. Removal of large amounts of biomass can be achieved by ensuring intimate mixing in the biomass separator unit, e.g., by the presence of mixing elements, whether static or dynamic, and/or by the use of a relatively large volume of aqueous medium, calculated on the volume of the slurry comprising biomass and solid fermentation product.

A waste stream comprising biomass is withdrawn from the top of the biomass separator unit. The biomass concentration in this effluent stream is determined completely by the amount of biomass present in the starting slurry, and by the volume of the aqueous medium provided to the unit. As a general value a range of 0.05 to 5 wt. % may be given.

The waste stream comprising biomass generally is a suspension of biomass in a solution of the fermentation product. The waste stream can be processed as desired. In one embodiment, the waste stream is subjected to a biomass removal step, e.g., by filtration, centrifugation, decantation, or combinations thereof. The remaining solution can, if so desired, be recycled as aqueous medium to the bottom of the biomass separator unit. It is noted that as the waste steam contains no, or only a very limited amount of solid fermentation product, biomass removal is not complicated.

The product stream comprising solid fermentation product can be processed as desired. It can, e.g., be subjected to a water removal step, optionally followed by washing and/or drying. It can also be processed as such. Where the product stream comprising solid fermentation product is subjected to a solid/liquid separation, e.g., in a filtration step, the resulting liquid can be recycled to the bottom of the biomass separator unit as part of the aqueous medium.

As indicated above, the fermentation broth comprising biomass and solid fermentation product may be provided directly from the fermentation unit to the separation step according to the invention. It is also possible, however, to carry out intermediate steps between the fermentation step and the separation step according to the invention. For example, the fermentation broth generated in the fermentation step may be provided to one or more previous biomass removal steps using, e.g., a hydrocyclone and/or a filter.

The nature of the solid fermentation product is not critical for the present invention. It can be any fermentation product which is present in the slurry at least partly in solid form, in other words, above its saturation concentration.

Examples of solid fermentation products include solid salts of carboxylic acids, in particular carboxylic acids selected from the group consisting of mono-, di-, and tricarboxylic acids having 2-8 carbon atoms. Preferably, the carboxylic acids do not contain amino-, or amido-groups. Examples of suitable carboxylic acids include lactic acid, propionic acid, citric acid, malic acid, maleic acid, fumaric acid, adipic acid, succinic acid, itaconic acid, tartaric acid, alpha-ketoglutaric acid, oxaloacetic acid, acetic acid, acrylic acid, 2-hydroxybutyric acid, 3-hydroxypropionic acid, and furandicarboxylic acid. Solid salts of lactic acid, succinic acid, fumaric acid, itaconic acid, adipic acid, 3-hydroxypropionic acid, and furan-dicarboxylic acid are considered preferred, with solid salts of lactic acid, succinic acid, and furandicarboxylic acid being considered particularly preferred.

Solid salts of these compounds generally are salts of divalent and trivalent cations including Mg, Ca, Zn, and Al, in particular Mg and Ca. Magnesium lactate, magnesium succinate, magnesium furandicarboxylate, calcium lactate, calcium succinate, and calcium furandicarboxylate are considered preferred, with the magnesium salts being particularly preferred, and magnesium lactate being specifically preferred.

Solid salts of carboxylic acids are generally obtained as fermentation products as follows: In the production of carboxylic acids in a fermentation process, an alkaline compound, e.g., an oxide, hydroxide, or carbonate compound, is often added to keep the pH of the fermentation broth in the range appropriate for the microorganism effecting the fermentation. In consequence, the acid is often present in the fermentation broth in the form of its salt. Depending on the nature of the alkaline compound, the salt may be dissolved in the fermentation broth or it may be present (in part) the solid form. Fermentation processes generating solid fermentation products, in particular solid salts of carboxylic acid, are known in the art and require no further elucidation here.

The solid fermentation products obtained by the method according to the invention can be processed as desired.

For example, it can be subjected to purification steps in manners known in the art, e.g., via washing of the solid fermentation product and/or recrystallisation, resulting in purified solid fermentation product.

Where the solid fermentation product is a solid salt of a carboxylic acid, it can, if so desired, be converted into the corresponding acid. This can be done by various methods, including an ion exchange method, e.g. by use of an ion exchange column or electrodialysis, or acidification using a strong inorganic acid (e.g. sulfuric acid, HCl or $HNO_3$) to provide a mixture of carboxylic acid and inorganic salt (e.g., calcium sulphate where a calcium salt of a carboxylic acid is converted to the corresponding acid by reaction with sulphuric acid, or magnesium chloride, where a magnesium salt of a carboxylic acid is converted to the corresponding acid by reaction with hydrochloric acid). This mixture can subsequently be subjected to an acid/salt separation step, resulting in the carboxylic acid being separated from the salt.

The separation step can be carried out by methods known in the art. Where the carboxylic acid is in solid form and the inorganic salt is in the dissolved form, a solid/liquid separation step can be carried out. The same applies where the carboxylic acid is in the dissolved form and the inorganic salt is in the solid form. Where carboxylic acid and the inorganic salt are both present in the dissolved state, the separation of the carboxylic acid from the inorganic salt solution can, e.g., be carried out by extracting the carboxylic acid from the salt solution using an organic extractant which is not miscible with the aqueous salt solution. The carboxylic acid can then be recovered from the extractant by, e.g., removing the extractant through evaporation, or by extracting the carboxylic acid from the extractant with water, resulting in the formation of an aqueous carboxylic acid solution.

Aqueous carboxylic acid solutions can be purified by methods known in the art, e.g., by treatment with active carbon. They can be concentrated by removal of water. The carboxylic acid can be purified, e.g., by distillation, resulting in a purified carboxylic acid. The carboxylic acid can be crystallised, if so desired, to form a solid crystalline carboxylic acid.

Other separation methods and purification methods are known in the art.

Where the carboxylic acid is lactic acid, e.g., obtained from calcium lactate and in particular magnesium lactate as solid fermentation product, it can, if so desired, be subjected to an oligomerisation step by removal of water, to form lactic acid oligomers. Where the carboxylic acid is lactic acid, it can, if so desired, be converted to lactide. The lactide, or the lactic acid itself, can be converted to polylactic acid.

The various methods for further treatment of solid fermentation product, conversion of carboxylic acid salts into the carboxylic acid, recovery of the carboxylic acid and further treatment thereof are conventional and require no further elucidation.

The invention will be elucidated by the following example, without being limited thereto or thereby.

EXAMPLE

Example 1

An aqueous slurry comprising magnesium lactate and biomass was obtained by subjecting a fermentation broth withdrawn from a fermentation reactor step to a concentration step. The slurry contained 56 wt. % of magnesium lactate and 0.12 wt. % of biomass. The slurry was provided continuously to the top of a biomass separator unit, which was equipped with a stirrer. An aqueous solution of magnesium lactate (8 wt. %, 100% of saturation concentration) was provided continuously to the bottom of the biomass separator unit. The aqueous medium was provided in an amount of 100 vol. % of the amount of aqueous slurry per unit of time.

A waste stream was withdrawn from the top of the biomass separator unit. The waste stream has a biomass content of 0.12 wt. % (the same as that of the starting slurry), and a magnesium lactate concentration of 8 wt. %.

A product stream comprising solid magnesium lactate was withdrawn from the bottom of the biomass separator unit. It has a magnesium lactate concentration of 59 wt. % and a biomass content of less than 0.01 wt. %, which is a reduction in biomass content of 98%. The product stream was provided to a filter to isolate solid magnesium lactate, which is washed with a magnesium lactate solution, and dried.

The invention claimed is:

1. A method for separating biomass from a solid fermentation product, comprising:
    providing an aqueous slurry comprising biomass and a solid fermentation product to an upper part of a biomass separator;
    providing an aqueous medium to a bottom of a biomass separator, while withdrawing a product stream comprising the solid fermentation product from the bottom of the biomass separator and withdrawing a waste stream comprising the biomass from the upper part of the biomass separator;
    contacting the aqueous slurry in countercurrent operation with the aqueous medium; and
    mixing the aqueous slurry and the aqueous medium during the contacting with one or more dynamic mixing elements.

2. The method according to claim 1, wherein the aqueous slurry comprises at least 10 wt. % of the solid fermentation product.

3. The method according to claim 1, wherein an amount of the biomass present in the aqueous slurry is in a range of 0.05 to 5 wt. %.

4. The method according to claim 3, wherein the amount of the biomass present in the aqueous slurry is in a range of 0.05 to 1.5 wt. %.

5. The method according to claim 1, wherein the aqueous medium is a solution of the fermentation product.

6. The method according to claim 1, further comprising:
    removing biomass from the waste stream, and
    recycling the remaining solution from the step of removing the biomass as aqueous medium to the bottom of the biomass separator.

7. The method according to claim 1, wherein the solid fermentation product is salts of carboxylic acids.

8. The method according to claim 1, further comprising purifying the solid fermentation product in the product stream to provide a purified solid fermentation product.

9. The method according to claim 1, wherein the solid fermentation product is a salt of a carboxylic acid, and the method further comprises converting the salt of the carboxylic acid into a corresponding carboxylic acid to form the carboxylic acid and an inorganic salt.

10. The method according to claim 9, further comprising separating the carboxylic acid from the inorganic salt.

11. The method according to claim 1, wherein the solid fermentation product is a solid lactic acid salt, the method further comprising:
    converting the solid lactic acid salt to lactic acid, and either:
    carrying out one or more of purifying, crystallizing or oligomerizing the lactic acid to form lactic acid oligomers, or converting the lactic acid to lactide, or to polylactic acid, either directly or via lactide.

12. The method according to claim 1, wherein the aqueous slurry comprises at most 70 wt. % of the solid fermentation product.

13. The method according to claim 1, wherein the aqueous slurry comprises at least 10 wt. % of the solid fermentation product to at most 70 wt. % of the solid fermentation product.

14. The method according to claim 3, wherein the amount of biomass present in the aqueous slurry is in a range of 0.05 to 1.0 wt. %.

15. The method according to claim 1, wherein the aqueous medium is at least 70% saturated with the fermentation product.

16. The method according to claim 1, wherein the aqueous medium is at least 50% saturated with the fermentation product.

17. The method according to claim 1, wherein the solid fermentation product is salts of carboxylic acids selected from the group consisting of magnesium lactate, magnesium succinate, magnesium furandicarboxylate, calcium lactate, calcium succinate, and calcium furandicarboxylate.

18. The method according to claim 1, wherein the solid fermentation product is magnesium lactate.

19. The method according to claim 1, wherein the aqueous slurry comprises at least 30 wt. % of the solid fermentation product and at most 60 wt. % of the solid fermentation product.

20. The method according to claim 1, wherein the volume of the aqueous medium provided to the biomass separator per unit of time is 10-100% of the volume of the aqueous slurry provided to the biomass separator per unit of time.

* * * * *